United States Patent [19]

Haga

[11] Patent Number: 5,583,632
[45] Date of Patent: Dec. 10, 1996

[54] APPARATUS FOR TWO OR THREE DIMENSIONAL OPTICAL INSPECTION OF A SAMPLE

[75] Inventor: Kazumi Haga, Chofu, Japan

[73] Assignee: New Creation Co., Ltd., Japan

[21] Appl. No.: 267,927

[22] Filed: Jul. 6, 1994

[30] Foreign Application Priority Data

Jun. 21, 1994 [JP] Japan .................................. 6-162848

[51] Int. Cl.⁶ .......................... G01N 21/41; G01N 21/00; G01B 11/30; G01B 9/02
[52] U.S. Cl. .......................... 356/129; 356/359; 356/362; 356/371; 356/237; 356/445
[58] Field of Search .................................. 356/129, 371, 356/237, 359, 362, 445

[56] References Cited

U.S. PATENT DOCUMENTS

| | | | |
|---|---|---|---|
| 3,782,836 | 1/1974 | Fey et al. | 356/237 |
| 3,815,998 | 6/1974 | Tietze | 356/237 |
| 4,215,939 | 8/1980 | Miller et al. | 356/371 |
| 4,326,808 | 4/1982 | Pryor et al. | 356/445 |
| 4,421,410 | 12/1983 | Karasaki | 356/237 |
| 4,459,023 | 7/1984 | Reich et al. | 356/237 |
| 4,643,540 | 2/1987 | Kawasaki et al. . | |
| 4,687,338 | 8/1987 | Task et al. | 356/237 |
| 4,854,708 | 8/1989 | Kafri et al. | 356/371 |
| 4,871,257 | 10/1989 | Suzuki et al. | 356/237 |
| 5,159,412 | 10/1992 | Willenborg et al. | 356/445 |
| 5,239,171 | 8/1993 | Takabayaski et al. | 356/73 |
| 5,286,943 | 2/1994 | Has . | |
| 5,305,054 | 4/1994 | Suzuki et al. | 355/53 |

FOREIGN PATENT DOCUMENTS

| | | | |
|---|---|---|---|
| 5-90366 | 4/1993 | Japan . | |
| 669184 | 6/1979 | U.S.S.R. | 356/129 |

OTHER PUBLICATIONS

Krasovskii et al, "The sensitivity threshold of an autocollimation television shadow graph" Sov. J. Opt Tech, vol. 41, No. 9, Sep. 1974. pp. 406–409.

Primary Examiner—Frank Gonzalez
Assistant Examiner—Jason D. Eisenberg
Attorney, Agent, or Firm—Evenson, McKeown, Edwards & Lenahan P.L.L.C.

[57] ABSTRACT

In an optical inspecting apparatus, first, a sample is illuminated with light. Then, an optical element causes light reflected from the sample or light transmitted through the sample to be focused, to thereby permit same to pass through an aperture stop arranged on a back focal plane or in its vicinity of the optical element. A telecenttic system converts the light having passed through the aperture stop into a parallel light. An image on the air formed by the telecentric system is viewed for inspection of the sample surface.

17 Claims, 4 Drawing Sheets

APPARATUS FOR TWO OR THREE DIMENSIONAL OPTICAL INSPECTION OF A SAMPLE

BACKGROUND OF THE INVENTION

1. Field of the Invention

This invention relates to an optical inspecting apparatus for two-dimensionally or three-dimensionally viewing a surface of a sample or the like, and more particularly to an optical inspecting apparatus of this kind which is suitable, e.g. for inspecting the state or condition of a surface (hereinafter referred to as a "sample surface") of a sample, such as a mirror-finished surface wafer, or for detecting a symbol, particularly an ID (identification) number (serial number as an identifier), formed on the sample surface.

2. Prior Art

Conventionally, an optical inspecting apparatus is used for checking the state of the sample surface for an undulation, a dimple, a projection, insufficient wash, or buff damage, or for detecting an ID number formed on a sample surface of a member used for manufacturing semiconductor integrated circuits, etc. The present applicant has already proposed an inspecting apparatus of this kind, which comprises (1) an illuminating optical system for illuminating a sample with light, (2) a schlieren optical system which includes an optical element for focusing light transmitted through the sample or light reflected from the sample, and has an aperture stop arranged on a back focal plane of the optical element or in its vicinity in an image space of same, and (3) a viewing block for viewing light having passed through the aperture stop (Japanese Provisional Patent Publication (Kokai) No. 6-3625).

The schlieren optical system used in the inspecting apparatus is one of typical optical systems for indicating variations in refractive index, reflectance, and transmittance resulting from the irregularities on the sample surface or the internal condition of the sample, as differences in brightness. This optical system is adapted to cause the light reflected from the sample surface to be focused by the collimator lens, and a knife edge arranged on a back focal plane of the collimator lens in an image space thereof intercepts scattered portions of the light reflected from the sample surface, permitting an image on the air of the sample surface, which is formed by the collimator lens in the air behind the collimator lens, to be viewed by the eye or by the use of a camera or other devices (a viewing block).

The term "image on the air" means a focused image formed in the air or on an imaginary plane perpendicular to an optical axis of a lens or lens system, at a predetermined location in its image space, which would be visible on a screen placed at the predetermined location. The predetermined location depends on the characteristics of the lens of the first telecentric system 17.

According to this optical system, if there is an irregularity on the sample surface, the light is scattered from the irregularity. Part of the scattered light from the irregularity hits against the knife edge, and is prevented from reaching the viewing block. As a result, when viewed from behind the knife edge, the portion (irregularity) of the sample surface corresponding to the scattered light intercepted by the knife edge becomes darker than the rest of the sample surface. A pattern of bright portions and dark portions corresponds to the state of the sample surface, and hence it is possible to judge the slate of the sample surface from this pattern.

However, these conventional optical inspecting apparatuses, including the proposed one, uniformly have the viewing block arranged in a location immediately behind the knife edge, where an image on the air is formed. Therefore, the position of the viewing block is not necessarily convenient to a viewer who views the image. Further, when a plurality of viewing blocks having different magnifications are to be provided, the viewing blocks are provided close to each other at the location where the image on the air is formed, so that the freedom of arrangement of these viewing blocks is very limited.

SUMMARY OF THE INVENTION

It is a first object of the invention to provide an optical inspecting apparatus which is capable of having viewing blocks arranged in respective locations permitting a viewer to view each image with ease.

It is a second object of the invention to provide an optical inspecting apparatus which is capable of having a plurality of viewing blocks having respective magnifications different from each other, freely arranged at desired locations.

To attain the above objects, the invention provides an optical inspecting apparatus comprising:

illuminating means for illuminating a sample with an illuminating light;

an optical element for focusing light reflected from the sample or transmitted through the sample;

an aperture stop arranged on or, in the vincinity of a back focal plane of the optical element in an image space thereof;

a telecentric system arranged on a back side of the aperture stop for converting light having passed through the aperture stop into a parallel light; and viewing means by which an image on the air formed by the telecentric system in the air is viewed.

According to the optical inspecting system of the invention, when a sample is illuminated by light, transmitted light having been transmitted through the sample or a reflected light reflected from same is focused by the optical element, and is transmitted via the aperture stop arranged on, or in the vincinity of the back focal plane the optical element, in the image space thereof, to the viewing means. As a result, an image of the sample can be viewed by the viewing means. In this case, the telecentric system arranged on the back side of the aperture stop converts the light having passed through the aperture stop into a parallel light, and forms an image on the air at a predetermined location depending on the focal length of the telecentric system. A viewer can observe the sample by focusing the viewing means to the image on the air. Therefore, the viewing means is not required to be arranged at a location where the image on the air is formed, but may be arranged at a desired location different from that of the image on the air so long as the viewing means can be focused to the image on the air. This makes it possible for a viewer to see an image of the sample from a position suitable for viewing the image.

Preferably, the viewing means includes at least one optical splitting element for splitting the parallel light, and a plurality of viewing blocks by which the image on the air is viewed based on split parallel light formed by the at least one optical splitting element.

According to this preferred embodiment, the optical splitting element splits the parallel light, and it is possible to view images on the air which are based on the split parallel lights split by the optical splitting element, by the respective viewing blocks, while changing magnification from one to another, if required. In this case, each of the plurality of viewing blocks can be set at desired locations that are displaced from the location where the image on the air is formed, so long as they can be focused to the images on the air. Therefore, even if a plurality of viewing blocks are to be provided, they can be arranged at locations from which the viewer can view with ease.

According to a preferred embodiment, the optical splitting element is formed by a prism, and hence compared with a half mirror and the like, it is possible to reduce loss of light which would otherwise occur when the parallel light is split, and also it is possible to minimize degradation of sensitivity of the apparatus, if there are provided a plurality of viewing blocks.

Further preferably, the illuminating means includes a laser beam source for emitting a laser beam, and an ordinary light source for emitting an ordinary light other than the laser beam, the optical splitting element having a selective filter for separating the laser beam and the ordinary light from each other, and at least one of the plurality of viewing blocks having means for causing moire fringes or other optical interference fringes to be generated in the image on the air formed based on the laser beam.

According to this preferred embodiment, the sample is illuminated with a laser beam and an ordinary light emitted from respective light sources. It is possible to view the sample based on respective transmitted lights or reflected lights The reflected or transmitted laser beam is separated from the reflected or transmitted ordinary light by the selective filter. An image on the air based on the separated laser beam is viewed by the viewing block while generating moire fringes or interference fringes. This makes it possible to view a three-dimensional state of the sample.

Preferably, the ordinary light emits a halogen light.

Preferably, the illuminating means includes a laser beam source for emitting a laser beam, and an ordinary light source for emitting an ordinary light other than the laser beam, the optical splitting element having a selective filter for separating the laser beam and the ordinary light from each other, at least one of the plurality of viewing blocks including a one-dimensional CCD for measuring an intensity distribution of the laser beam.

According to this preferred embodiment, the image on the air based on the laser beam separated by the selective filter can be viewed by means of the one-dimensional CCD. Since the laser beam has a single wavelength which is short, it is possible to obtain information on subtle irregularities on the sample, based on transmitted or reflected laser beam obtained therefrom, so that it is possible to accurately measure a peak-to-valley of such irregularities.

Preferably, the viewing means includes image rotation means for rotating the image on the air, and for presenting the resulting one of the image on the air rotated by the image rotating means.

According to this preferred embodiment, it is possible to view a desired portion of the sample surface without shifting the position of the sample, by rotating the image on the air by the image rotation means. Further, when viewing an ID number or the like formed on the sample surface, the sample can be turned in a desired direction, and hence it is possible to set an image of the ID number in such a direction as enables the viewer to read it with telecentric system for focusing the parallel light.

According to a preferred embodiment, the viewing means includes a telecentric system for causing the parallel light to be focused. Therefore, even if the focusing is insufficient to some degree, it is possible to view the image on the air without changing the magnification.

Preferably, the viewing means includes an image pick-up element for picking up the image on the air, and an image processing block for performing image processing based on an image signal delivered from the image pick-up element.

According to this preferred embodiment, the image processing block performs image processing based on the image signal from the image pick-up element. Therefore, it is possible, for example, to determine a peak-to-valley of an irregularity of the sample, or to observe the sample by a clearer image thereof.

Preferably, the optical inspecting apparatus further comprises a light level control signal-generating means for generating a light level control signal for setting a white level voltage or a black level voltage in the image signal to a predetermined value, and a light level control block for changing a level of light emitted from the illuminating means based on the light level control signal.

According to this preferred embodiment, in response to the light level control signal delivered from the light level control signal-generating means, the light level control block controls the level of the light emitted from the illuminating means such that the white level voltage or the black level voltage in the image signal is equal to a predetermined value. Therefore, the level of the image signal is prevented from being saturated, which permits the sample to be viewed under a suitable condition.

The above and other objects, features, and advantages of the invention will become more apparent from the following detailed description taken in conjunction of the accompanying drawings.

DETAILED DESCRIPTION

Next, the invention will be described in detail with reference to drawings showing preferred embodiments thereof.

Figure 1:
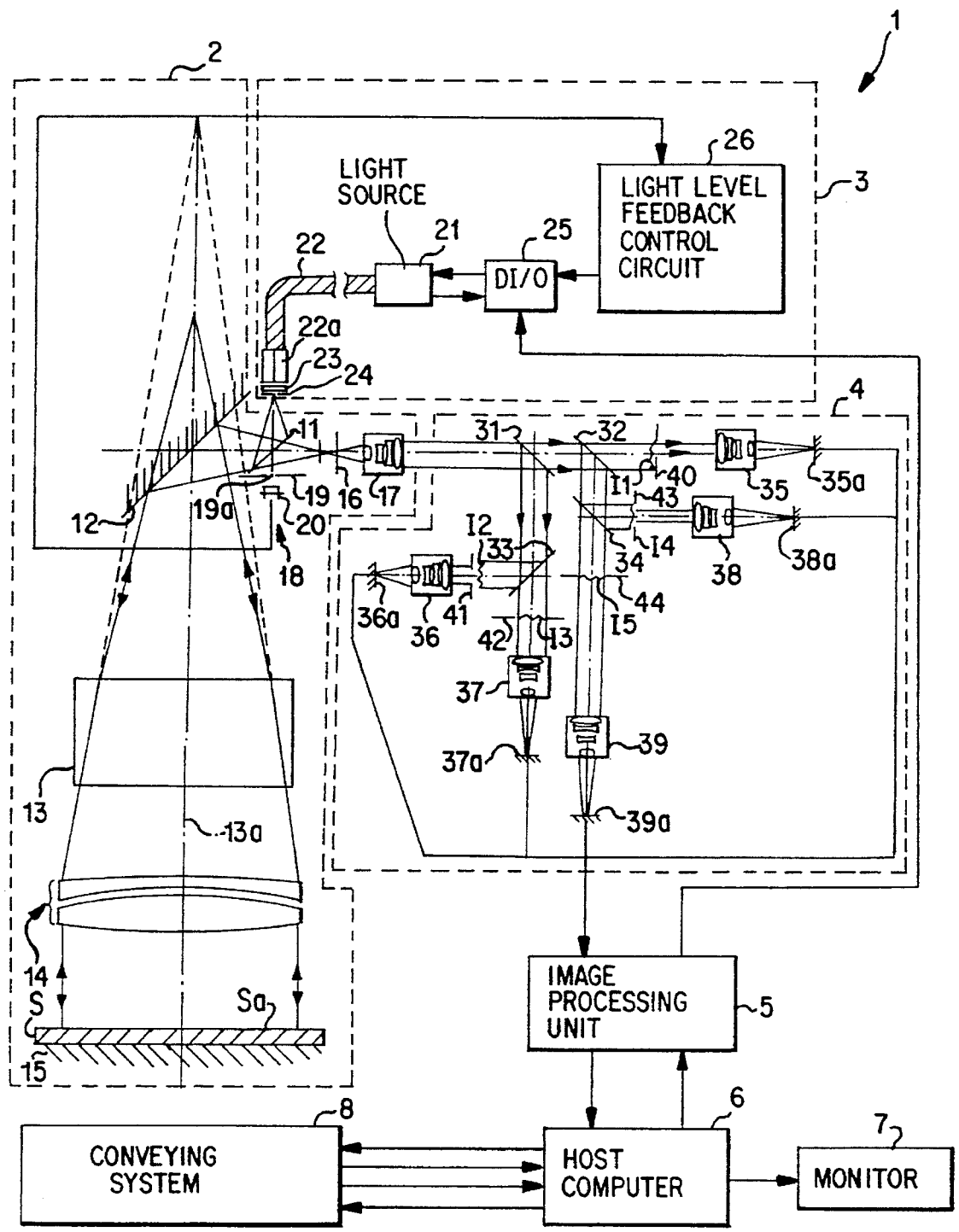
FIG. 1 is a block diagram showing the whole arrangement of an optical inspecting apparatus according to a first embodiment of the invention.

Referring first to FIG. 1, reference numeral 1 generally designates an optical inspecting apparatus according to a first embodiment of the invention. The optical inspecting apparatus 1 is mainly comprised of an optical system block 2, a light source block 3, a viewing block 4, an image processing unit 5, a host computer 6, a monitor 7, and a conveying system 8.

Now, an outline of the optical inspecting apparatus 1 will be described. An illuminating light emitted from the light source block 3 is caused to illuminate a sample surface Sa of a sample S placed within the optical system block 2, in a normal direction, i.e. in a direction perpendicular to the sample surface Sa. The light reflected from the sample surface Sa travels in a direction opposite to that of the illuminating light, and is focused by the optical system block 2 to pass through a knife edge 16. The light transmitted through the knife edge 16 is detected and converted by a CCD (charge-coupled device) into an image signal. Scattered light from the sample surface Sa is intercepted by the knife edge 16 and hence prevented from entering the CCD. Therefore, light reflected from a portion of the sample surface Sa in a scattered manner is converted into a signal indicative of a dark portion in a pattern of the image of an illuminated part of the sample, whereas light reflected normally or in a direction perpendicular to the sample surface is converted into a signal indicative of a bright portion of the pattern of the image. The image signal is then processed by the image processing unit 5 and then displayed via the host computer 6 on the monitor 7.

Next, each block and unit of the optical inspecting apparatus will be described.

The optical system block 2 illuminates the sample S, such as a semiconductor wafer, with light, and receives the light reflected from the sample surface Sa, based on which irregularities or an ID number on the sample are viewed. The optical system block 2 is comprised of a first half mirror 11, a reflecting mirror 12, a lens unit (optical element) 13, a collimator lens system (optical element) 14, a tilting stage 15, a knife edge (aperture stop) 16, a first telecentric system 17, and a light level feedback block 18.

The first half mirror 11 is inclined through 45° with respect to an optical axis (axis of a light path) 13a, and reflects illuminating light from the light source block 3 toward the reflecting mirror 12, and at the same time permits reflected light from the reflecting mirror 12 to pass therethrough to the viewing block 4.

The reflecting mirror 12 reflects light transmitted from the half mirror 11 toward the tilting stage 15, and at the same time reflects light reflected from the sample S toward the viewing block 4.

The lens unit 13 is comprised of two lenses, and has a function of reducing a focal length of the collimator lens system 14. This makes it possible to reduce the distance between the tilting stage 15 and the reflecting mirror 12, and the distance between the optical system block 2 and the viewing block 4, which contributes to reduction of the size of the optical inspecting apparatus 1.

The collimator lens system 14 converts the illuminating light transmitted from the light source block 3 into a parallel beam, and at the same time converts the parallel light reflected from the sample S into a converging beam.

The tilting stage 15 is a table on which the sample S is placed. The conveying system 8 conveys the sample S to the tilting stage 15. The titling stage 15 is constructed such that it is capable of finely adjusting an inclination of the sample S so as to cause the illuminating light to normally or perpendicularly enter the sample surface Sa.

The knife edge 16 is a stop aperture of a biaxially-crossed type equipped with an opening/closing mechanism, which is arranged on a back focal plane of the collimator lens system 14 in an image space thereof for eliminating undesired scattered light reflected from irregularities formed on the sample surface Sa of the sample S. The knife edge 16, the lens system unit 13, and the collimator lens 14 form a schlieren system.

The first telecentric system 17 is comprised of five lenses, and converts the reflected light, which is focused and transmitted through the knife edge 16, into parallel light, thereby forming an image on the air on its optical axis on a back side thereof.

The light level feedback block 18 controls the level of light emitted from a light source 21, and is comprised of a shield board 19 and a photodetector 20. The shield board 19 is formed with a pinhole 19a for permitting illuminating light to pass therethrough. The photodetector 20 detects the light level of the illuminating light having passed through the pinhole 19a, and delivers a signal indicative of data of light level detected to a light level feedback control block 26.

Now, the light source block 3 will be described. The light source block 3 generates and emits illuminating light for illuminating the sample S, and is comprised of the light source 21, a light guide fiber 22, a wavelength-selecting filter 23, a pinhole 24, DI/O (digital I/O) 25, and the light level feedback control circuit 26.

The light sources 21 is equipped with a halogen lamp. The level of light emitted from the halogen lamp is feedback-controlled to a predetermined value by the light level feedback control circuit 26 such that a level of light detected by the photodetector 20 becomes equal to a predetermined value. In this connection, a lamp used as the light source 21 is not limited to the halogen lamp, but it is possible to use various kinds of electric-discharge tubes, including a xenon lamp and a metal halide lamp, depending on the nature of an object of inspection.

The light guide fiber 22 is formed of a bundle of optical fibers and is provided with a light conducting rod 22a on a front end thereof. The light conducting rod 22a diverges light transmitted through the light guide fiber 22, and also deletes dot images formed of an end face of the bundle of optical fibers constituting the light guide fiber. The light guide fiber 22 may be formed of a single optical fiber.

The wavelength-selecting filter 23 selects a wavelength of illuminating light for illuminating the sample surface Sa. The wavelength-selecting filter 23 is in the form of a turret equipped with a various types of interference filters, making it possible to properly change the wavelength of the illuminating light for illuminating the sample surface Sa. The wavelength-selecting filter 23 is also used in adjusting the sensitivity of optical systems of the optical inspecting apparatus 1. For example, when a peak-to-valley value related to irregularities on the sample surface Sa is small, a shorter wavelength band is selected.

The pinhole 24 converts the halogen light into the illuminating light having a predetermined diverging angle. The diverging angle of the illuminating light emitted from an opening of the pinhole 24 must be adjusted to agree with an area of the sample surface Sa to be illuminated. This adjustment is effected by adjusting the distance between the light conducting rod 22a and the pin hole 24.

The DI/O 25 is an interface circuit for delivering a light level control signal as parallel data output from the light level feedback control circuit 26 and the image processing unit 5, to the light source 21, to thereby control the level of light emitted from the light source 21.

The light level feedback control circuit 26 converts a light level signal of an analog type delivered from the light level feedback block 18 into digital light level data indicative of the light level, and at the same time controls the level of light from the light source 21 via the DI/O 25 such that the digital light level data becomes equal to reference light level data. Thus, the level of light emitted from the light source 21 is feedback-controlled to a predetermined value.

Next, the viewing block 4 will be described in detail. The viewing block 4 includes second to fifth half mirrors 31 to 34, second to sixth telecentric systems 35 to 39, CCD's (charge-coupled devices) 35a to 39a, and apertures 40 to 44.

The second to sixth half mirrors 31 to 34 each reflect approximately half of light received, and permit the remainder of approximately half of the light received to pass therethrough, whereby the reflected light received from the first telecentric system 17 or a split portion thereof is split into two respective branched light paths.

The second to sixth telecentric systems 35 to 39 detect images of portions of the illuminated area of the sample surface Sa based on the light reflected from the sample surface Sa, each of which is comprised of five lenses and a focusing mechanism, not shown, for adjusting the focus to an image on the air. The second to fifth telecentric systems 35 to 38 serve as viewing sections for a higher magnification and are each adapted to be capable of viewing a portion of the illuminated area of the sample surface Sa in an enlarged scale. More specifically, the second to fifth telecentric systems 35 to 38 permit images based on light having passed through the apertures 40 to 43 to be picked up by the CCD's 35a to 38a formed of 512×512 pixels, respectively. That is, although the CCD's 35a to 38a are constructed identical to a CCD 39a, they each pick up an image based on a reduced portion of reflected light corresponding to each reduced portion of the illuminated area of the sample surface Sa, and hence, in actuality, it is made possible to view the sample surface with a higher magnification. On the other hand, the sixth telecentric system 39 operates as a viewing section for a lower magnification, and permits an image of the whole illuminated area of the sample surface Sa based on the whole extension of light transmitted through the fourth half mirror 34 to be detected by the CCD 39a. Image signals delivered from the CCD's 35a to 39a are all delivered to the image processing unit 5.

The apertures 40 to 44 are arranged at locations where respective images I1 to I5 on the air are formed, for intercepting undesired light, such as scattered light from the sample surface Sa and noise, and for setting ranges of portions of the area of the sample surface Sa to be viewed by the second to sixth telecentric systems 35 to 39, respectively.

Next, the image processing unit 5 will be described in detail. The image processing unit 5 amplifies image signals delivered from CCD's (charge-coupled devices) 35a to 39a arranged within the viewing block 4, and then converts the resulting signals into digital signals to deliver same as digital image signals to the host computer 6. The image processing unit 5 also delivers a light level control signal to the DI/O 25 such that the white level voltage (voltage of the image signal at which the maximum brightness of the images is reached) falls within a predetermined range, i.e. for prevention of saturation of the white level voltage, to thereby control the level of light emitted from the light source 21. More specifically, the image processing unit 5 delivers the light level control signal formed in 8-bit parallel data to the DI/O 25 to thereby control the voltage applied to the light source 21, for control of the level of light emitted therefrom. As a result, it is possible to view the sample S without saturation of the image signal level.

The host computer 6 checks for irregularities on the sample surface Sa or detects an ID number formed on same based on the digital image signals delivered from the image processing unit 5. More specifically, the host computer 6 detects the size of irregularities (convexes and concaves) to determine whether the sample has an acceptable quality, and detects the ID number formed on the sample surface Sa, based on which checks are made on the steps of manufacturing semiconductor wafers, while performing various kinds of statistical processing. Further, the host computer 6, upon recognition of the ID number of the sample, starts to perform control to drive the conveying system 8, comprised of a conveyor belt, for conveying a subsequent sample S to the tilting stage 15. The optical inspecting apparatus may be constructed such that the conveying system 8 is directly controlled by the image processing unit 5.

Next, the operation of the optical inspecting apparatus according to the first embodiment will be described.

The light from the light source 21 is transmitted through the light guide fiber 22, and after being subjected to wavelength selection by the wavelength-selecting filter 23, caused to pass through the pinhole 24. The pinhole 24 converts the light into a diverging light by allowing the light to pass therethrough. The diverging light is reflected from the half mirror 11 and then from the reflecting mirror 12 to be transmitted through the lens unit 13. The light is then converted into parallel light by the collimator lens system 14, which illuminates the sample surface Sa. The light illuminating the sample surface Sa is reflected therefrom to travel toward the collimator lens system 14. If there is any irregularity (a convex, a concave, or the like) on the sample surface Sa, the light cast on the irregularity is reflected therefrom in a scattered manner.

The reflected light including part of the scattered light, if any, is subjected to focusing by the collimator lens system 14, and then reflected by the reflecting mirror 12. The light reflected from the reflecting mirror 12 passes through the half mirror 11 to travel to the knife edge 16, which intercepts the part of the scattered light reflected from the irregularity on the sample surface Sa. The remainder of the light, which is allowed to pass through the knife edge 16, is converted into the parallel light by the first telecentric system 17, and then transmitted to the second half mirror 31, where the parallel light is split into two light paths by reflection therefrom and transmission therethrough. Based on these split parallel light beam, images in the air are formed at respective locations. (It should be noted that parallel light formed by a telecentric system means a light in which major light beam rays are parallel to its optical axis).

By focusing the second to sixth telecentric systems 35 to 39 to form an image on the air, the image on the air is picked up by the CCD's 35a to 39a, respectively. If there are irregularities on the sample surface Sa, portions of the scattered light reflected from the irregularities are intercepted by the knife edge 16, and hence the CCD's 35a to 39a pick up images of respective portions of the illuminated area of the sample surface Sa in a pattern wherein the irregularities are presented as dark portions and the remaining flat part is presented as a bright part.

Figure 2:
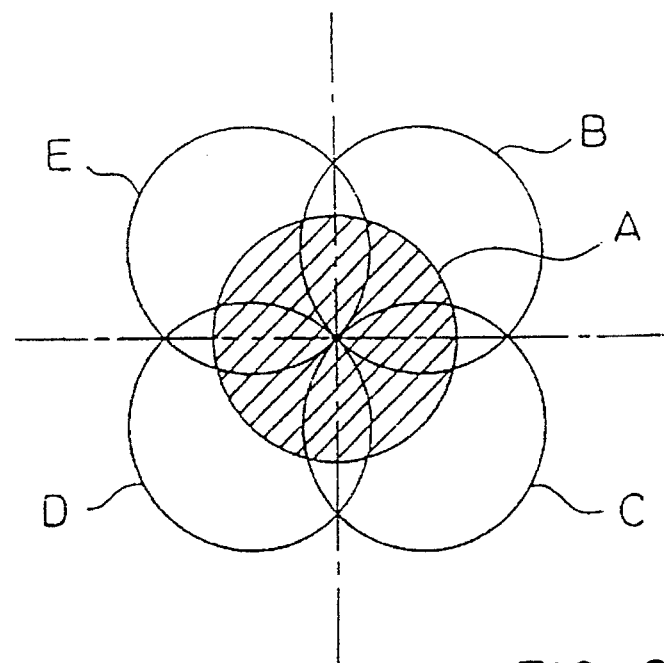
FIG. 2 is a diagram showing ranges of areas of an object to be viewed from which images are formed by respective CCD's.

Next, the ranges of the sample surface covered by images picked up by the CCD's 35a to 39a will be described. The CCD 39a picks up an image of the whole illuminated area of the sample surface Sa at a time. On the other hand, the CCD's 35a to 38a are reduced in the range of extension of light covering an illuminated area of the sample surface, from which each image is formed, and this reduced range of extension of light is picked up by the whole of each of the CCD's 35a to 38a, whereby in actuality portions of the sample surface Sa are viewed respectively in enlarged scales. The images picked up by the CCD's 35a to 38a are synthesized into a portion (hatched area) of the image of the sample surface Sa designated by a symbol A in FIG. 2, which corresponds to an object area of the sample surface Sa. In other words, symbols B to E designate portions of the sample surface on which respective images are formed by the CCD's 35a and 38a. The image processing unit 5 synthesizes these images to form an image of the object area A as an image of a portion of the sample surface in an enlarged scale.

As described heretofore, according to the first embodiment, a plurality of telecentric systems 35 to 39 with different magnifications and the CCD's 35a to 39a can be freely arranged at desired locations, respectively. Further, each of the CCD 35a to 39a picks up an image of a portion of the sample surface Sa by the whole pixels thereof, which makes it possible to view an enlarged image of a portion of the sample surface Sa. In addition, the image processing unit 5 parallel processes the five image signals, whereby it is possible to reduce the processing time required in obtaining processed image signals of one sample S.

Figure 3:
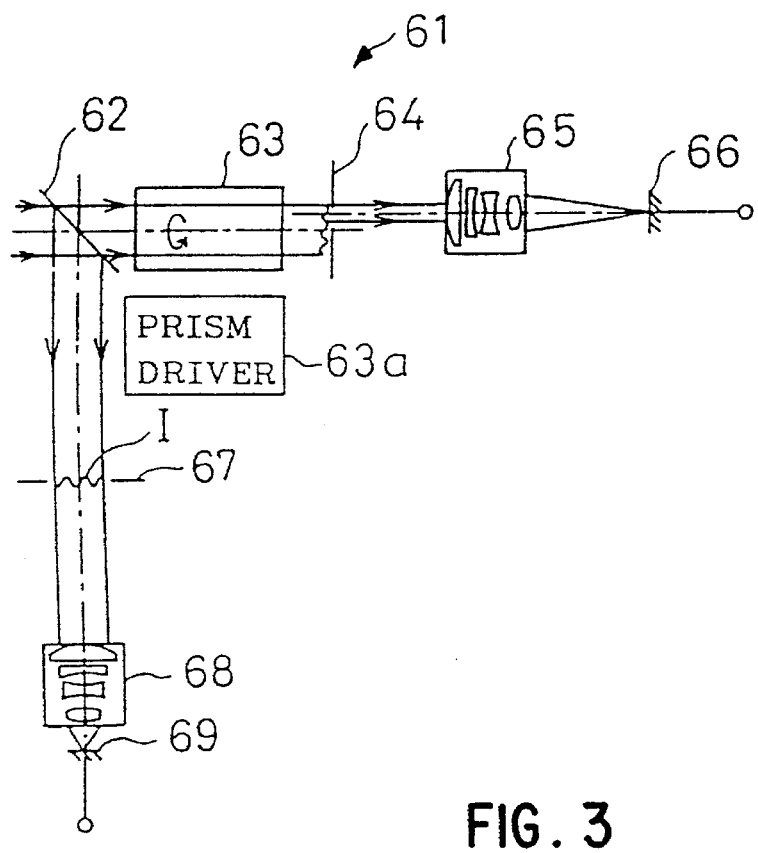
FIG. 3 is a diagram showing the arrangement of a viewing block of an optical inspecting apparatus according to a second embodiment of the invention.

Next, a second embodiment of the invention will be described with reference to FIG. 3.

This embodiment is distinguished from the first embodiment in respect of the arrangement of the viewing block 4, with remainder of the whole arrangement being similar to that of the first embodiment. As shown in FIG. 3, a viewing block 61 of the second embodiment is comprised of a half mirror 62, a dove prism 63, a first aperture 64, a telecentric system 65 for higher magnification, a first CCD 66, a second aperture 67, a telecentric system 68 for a lower magnification, and a second CCD 69.

The half mirror 62 split light received from the first telecentric system 17 arranged on its entrance side, by reflection therefrom and transmission therethrough.

The dove prism 63 is a so-called image rotation prism which has its cross-section transverse to a longitudinal section formed in the shape of a trapezoid. The dove prism 63 permits the parallel light to pass therethrough, thereby causing an image appearing on the output side thereof to rotate through an angle twice the angle of rotation of the dove prism 63. A prism driver 63a is provided for causing the prism 63 to rotate, and the prism driver 63a is controlled by the image processing unit 5 in respect of its rotating operation.

The first aperture 64 and the second aperture 67 are arranged at respective locations where images on the air are formed by the first telecentric system 17. Further, the first aperture 64 is restricted in its width such that only part of light emitted from the output side of the dove prism 63 is permitted to pass therethrough. As a result, the first CCD 66 is capable of picking up an enlarged image of part of the image on the air. The second aperture 67 is constructed such that it can be adjusted in its width, whereby the whole of the image of the air can be picked up by the second CCD 69.

The telecentric systems 65 and 68 are constructed identical to the telecentric systems 35 to 39 of the first embodiment.

Next, the operation of the second embodiment will be described. Since the component parts and elements of the second embodiment are identical to those of the first embodiment except for the viewing block 61, and hence only the operation of the viewing block 61 will be described.

Out of the parallel light emitted from the first telecentric system 17, a portion transmitted through the half mirror 62 enters the dove prism 63. In this case, a portion of the image on the air is picked up by the first CCD 66, and hence compared with a case in which the whole image on the air is picked up by a CCD having the same number of pixels, the area of a portion of the image on the air picked up per unit pixel is reduced, which in actuality makes it possible to pick up an enlarged image with high sensitivity. Further, a half rotation of the dove prism 63 causes one rotation of the image on the air, which makes it possible to promptly pick up an image of a desired portion of the sample surface Sa.

One other method of picking up an image with high sensitivity by the use of a CCD having an identical size and an identical number of pixels is to place the sample S on a sample stage which can be moved in X-Y directions perpendicular to each other, and move the sample stage in an X direction and a Y direction to view an enlarged image of each portion of the sample surface Sa. According to this method, to view the whole of the sample surface Sa, the sample stage is required to be moved in the X direction and in the Y direction many times, which is very troublesome. In contrast, according to the present embodiment, by rotating the dove prism 63, an image can be continuously picked up by the first CCD 66 on each portion of the sample surface Sa, which makes it possible to reduce the time required in imaging the whole illuminated area of the sample surface Sa, to a very short time period. It goes without saying that in this embodiment as well, the telecentric system 69 for a lower magnification provides an image of the whole illuminated area at the same time.

Figure 4:
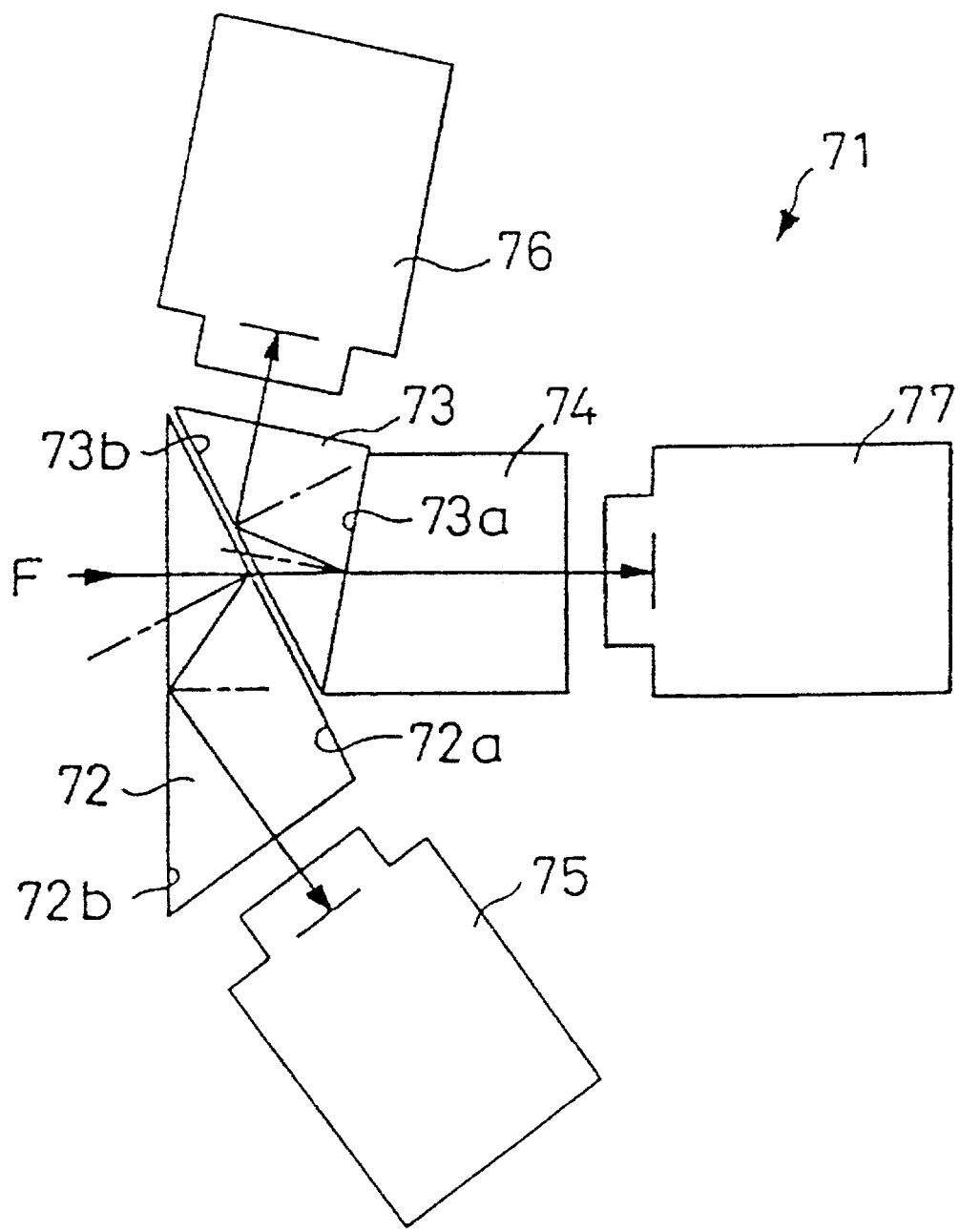
FIG. 4 is a diagram showing the arrangement of a viewing block of an optical inspecting apparatus according to a third embodiment of the invention.

Next, a third embodiment of the invention will be described with reference to FIG. 4.

This embodiment is distinguished from the first embodiment in respect of the arrangement of the viewing block 4, with remainder of the whole arrangement being similar to that of the first embodiment. As shown in FIG. 4, a viewing block 71 of the third embodiment is comprised of three prisms 72 to 74, a CCD 75 formed by a ⅓-inch CCD, a CCD 76 formed by a ½inch CCD, and a CCD 77 formed by a ⅔-inch CCD. Interposed between the first prism 72 and the first telecentric system 17, is a telecentric system (which is not particularly limited, and can be implemented by any focusing lens), not shown, for collecting the parallel light obtained by the first telecentric system 17 to transmit same to the prism 72.

The prism 72 permits part of the light received from a direction F (from the first telecentric system 17) to pass through an end face 72a, and reflects the rest of the light therefrom. The portion of the light reflected from the end face 72a is caused to be reflected from an end face 72b. The prism 73 permits part of the light having passed through the prism 72 to pass therethrough and reflects the rest of the light from an end face 73a. The light reflected from the end face 73a is further reflected from an end face 73b. The prism 74 is constructed such that it permits all the light having passed through the prism 73 to pass straight therethrough. As a result, when the light enters the viewing block 71, it is split and guided into three light paths. The divisional portions of the light enter the CCD's 75 to 77, respectively. The CCD's are each arranged at locations where the image on the air is formed by the first telecentric system 17 to pick up a focused image of the image on the air.

According to the third embodiment, the parallel light received from the first telecentric system 17 is split and guided into the three branches of the light path by the prisms 72 to 74, which makes it unnecessary to provide the half mirror(s) used in the first embodiment and the second embodiment. Therefore, loss (which would amount to 20%) of light which would occur when light is split by the use of a half mirror, is reduced to zero, so that it is possible to prevent lowering of sensitivity of the apparatus as much as possible, which lowering occurs when a plurality of viewing blocks are employed. Further, the sizes of the CCD's 75 to 77 are different from each other, so that it is possible to view the sample S by different magnifications at the same time. In this case, it is possible to view a central portion of the object of observation by different magnifications through alignment of the center of the CCD's 75 to 77 with the optical axis of the incident light, and also to view different areas of the object of the observation with different magnifications, by shifting the CCD's 75 to 77 by means of a shift mechanism provided therefor. The above arrangement characteristic of the third embodiment facilitates allocation of devices to their suitable locations, as well as contributes to reduction of manufacturing cost.

Figure 5:
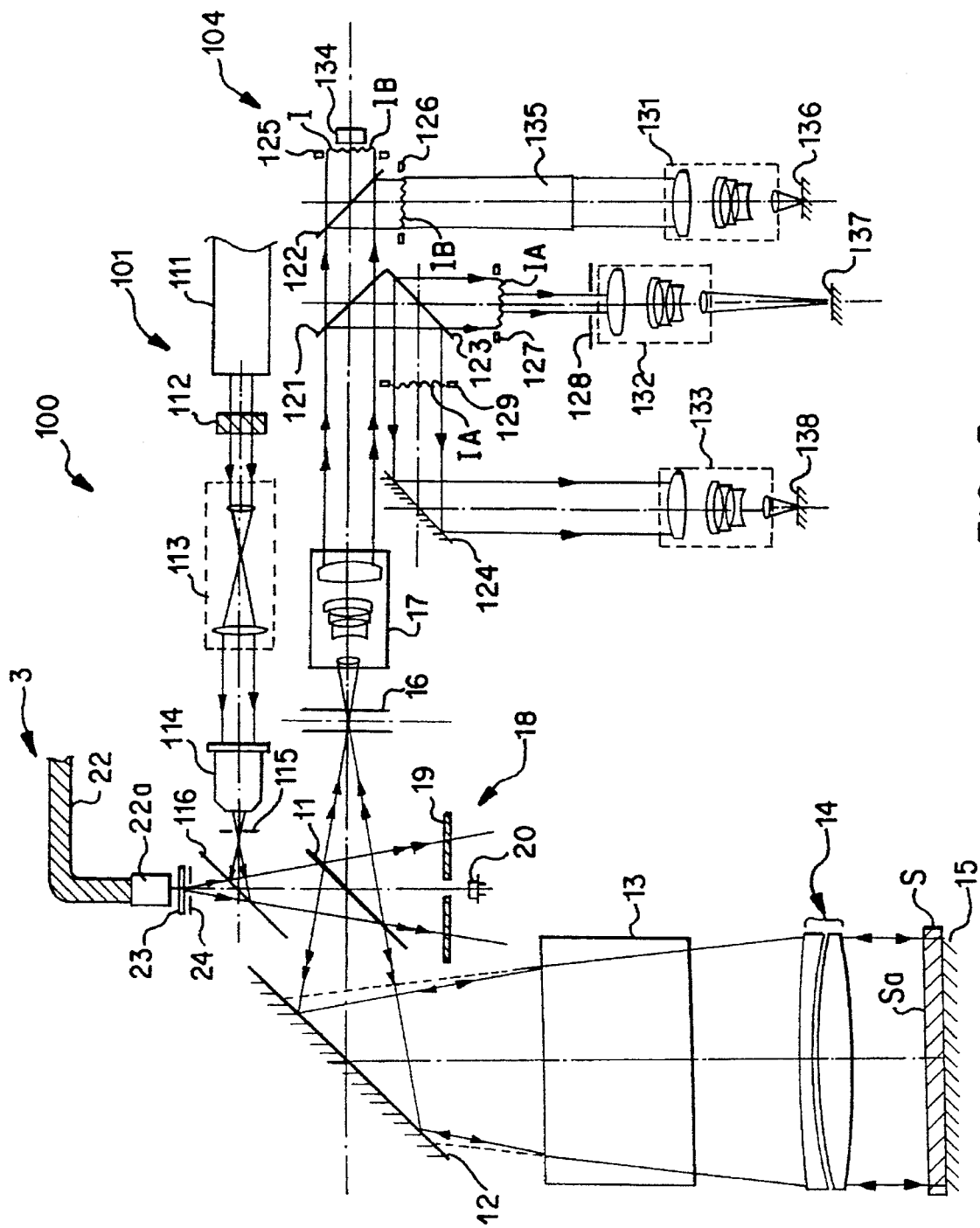
FIG. 5 is a diagram showing the arrangement of a viewing block of an optical inspecting apparatus according to a fourth embodiment of the invention.

Next, a fourth embodiment of the invention will be described with reference to FIG. 5.

An optical inspecting apparatus according to the present embodiment is distinguished from the first embodiment in that in addition to the light source 21, there is provided a light source 101 for emitting a He—Ne (helium-neon) laser beam, and that the viewing block 104 of this embodiment has an arrangement different from that of a corresponding block (viewing block 4) of the first embodiment. Component parts and elements identical to those of the first embodiment are designated by identical reference numerals, and detailed description thereof is omitted.

The optical inspecting apparatus 100 of the fourth embodiment illuminates both halogen light and laser beam on the sample S. The light cast on the sample S is reflected from the sample surface Sa, and the reflected light is separated by the viewing block 104 into the halogen light and the laser beam. An image on the air formed by the halogen light is picked up into an image signal, based on which a real-time image is displayed on the monitor 7. On the other hand, an image on the air formed by the laser beam is picked up into another image signal, which is subjected to signal processing at the image processing block 5 to form a video signal. The host computer 6 measures sizes of small irregularities formed on the sample surface Sa, and an undulation thereof, based on the video signal.

Next, the component parts and elements of the fourth embodiment will be described in detail.

First, the light source 101 will be described. The light source 101 is provided in addition to the light source block 3, and is comprised of a He—Ne laser 111, an acousto-optic modulator 112, a beam expander 113, an objective lens 114, a pinhole 115, and a half mirror 116.

The He—Ne laser 111 emits a laser beam having a single wavelength of 632.8 nm, and used as a measuring light source for measuring a peak-to-valley of an irregularity of the sample S, etc.

The acousto-optic modulator (AOM) 112 prevents a disturbance due to noise.

The beam expander 113 is comprised of two convex lenses, and the diameter of a laser beam emitted from the He—Ne laser 111 is increased according to the diameter of the objective lens 114.

The objective lens 114 collects parallel light emitted from the beam expander 113.

The pinhole 115 is arranged on a back focal plane of the objective lens 14 in its image space, and converts light, which is permitted to pass therethrough, into an illuminating light having a predetermined diverging angle.

Next, the viewing block 104 will be described. The viewing block 104 is comprised of first to third half mirrors 121 to 123, a reflecting mirror 124, first to fifth apertures 125 to 129, first to three telecentric systems 131 to 133, a one-dimensional CCD 134, a three-dimensional measuring optical unit 135, and first to third CCD's 136 to 138.

The first half mirror 121 is a so-called dichroic filter which reflects only the halogen light contained in the parallel light transmitted from the first telecentric system 17, and at the same time permits only the laser beam contained therein and generated from the light source 104 to pass therethrough. The second half mirror 122 splits and guides the laser beam into two light paths, by reflection therefrom and transmission therethrough. The third half mirror 123 splits and guides the halogen light from the first half mirror 121 into two light paths, by reflection therefrom and transmission therethrough. The reflecting mirror 124 further reflects the halogen light reflected from the half mirror 123 toward the third telecentric system 133.

The first to fifth apertures 125 to 129 intercept undesired light, such as scattered light reflected from the sample surface in a scattered manner, and noise.

The one-dimensional CCD 134 is formed by approximately 500 CCD elements arranged in a single line for measuring an intensity distribution of the laser beam, and is vertically scanned as viewed from the figure to generate information of brightness and darkness as one-dimensional data concerning the light reflected from the sample surface Sa.

The three-dimensional measuring optical unit 135 is comprised of internal two gratings for allowing light to pass between them to generate so-called moire fringes. The light processed for forming moire fringes is transmitted to the first telecentric system 131 and an image is picked up therefrom by the first CCD 136 to generate an image signal. The image signal generated by the first CCD 136 is suitable e.g. for macroscopically viewing an undulation on the sample surface, and is delivered to the image processing unit 5 for signal processing, from which the processed image signal is delivered via the computer 6 to the monitor 7 as a video signal. As a result, the monitor 7 displays a picture of an undulation or the like formed on the sample surface Sa as a pattern of brightness and darkness. In this connection, instead of the moire fringes, optical interference fringes may be used for forming the pattern of brightness and darkness.

The second telecentric system 132 is provided for viewing a portion of the image of the illustrated area of the sample surface Sa in an enlarged scale or magnified manner. The second telecentric system 132, the fourth aperture 128, and the second CCD 137 may be shifted without changing the positional relationship between them, relative to an image IA, referred to hereinafter, in the air in X-Y directions. As a result, the viewer can observe a desired portion of the image IA on the air based on the image signal from the second CCD 137. Shifting means, not shown, is provided for shifting the position of these devices in X-Y directions perpendicular to each other.

The third telecentric system 138 is provided for viewing a real-time image of the whole illustrated area of the sample surface Sa.

The operation of the optical inspecting apparatus 100 according to the fourth embodiment will be described.

In this apparatus, the halogen light emitted from the light source 21 is transmitted through the half mirror 116, while the laser beam emitted from the He—Ne laser 111 is reflected from the half mirror 116 to form a composite light which illuminates the sample S. Light reflected from the sample surface Sa is transmitted to the first telecenttic system 17, reversely following the light path of the illuminating light at least up to the half mirror, to be converted into parallel light, based on which an image on the air is formed at a predetermined location. In this case, the first half mirror 121 separates the halogen light and the laser beam from each other, and an image IA on the air based on the halogen light is formed on the front side of the first half mirror 121, while an image IB on the air based on the laser beam is formed on the back side of same.

In this case, the image IA on the air is suitable for viewing a real-time image of the sample surface Sa. On the other hand, the image IB on the air, which is formed based on the laser beam having a single wavelength, contains less undesired light than the image IA on the air formed based on the halogen light having various ranges of wavelength. Therefore, the image IB gives a clear image of small irregularities, an undulation, etc. formed in the illustrated area of the sample surface as the object to be viewed, which is displayed on the monitor, and based on which the host computer 6 is capable of measuring the size of these irregularities and the like.

The invention has been described heretofore based on preferred embodiments thereof shown only by way of example, and is by no means limited to such embodiments, but various modifications and variation can be made thereto without departing from the scope of the invention defined by claims appended hereto.

For example, although in the above embodiment, description has been made of cases where the light reflected from the sample is detected, this is not limitative, but it goes without saying that the present invention, which comprises illuminating means for illuminating a sample with an illuminating light, an optical element for focusing a reflected light reflected from the sample or a transmitted light having been transmitted through the sample, a aperture stop arranged on a back focal plane or in its vicinity of the optical element in an image space thereof, a telecentric system arranged on a back side of the aperture stop for converting light having passed through the aperture stop into a parallel light, and viewing means by which an image on the air formed by the telecentric system in the air is viewed, can also be applied to an apparatus for detecting light transmitted through the sample, thereby achieving the advantageous results described hereinabove, particularly, in this case, the advantageous results in detecting the state of the inside of the sample.

Further, the dove prism 63 of the second embodiment may be arranged before the telecentric systems 35 to 38 of the first embodiment, or before the one-dimensional CCD 134 of the fourth embodiment. The component parts or elements of the embodiment may be used in combination as desired.

Further, although in the above embodiment, the wavelength-selecting filter 23 is used, an ND filter (neutral density filter) may be provided in addition to or in place of the wavelength-selecting filter 23. The ND filter is used for the purpose of attenuating light without changing the spectrum characteristics of the light received. The light attenuation is required e.g. in detecting an undulation of the sample surface Sa. In detecting a gentle change in the surface configuration, such as an undulation, normally-reflected components of the light are much increased, which makes the sample surface too bright, and hence the whole image formed by the reflected light becomes so bright that it is difficult to view the image, unless the illuminating light is attenuated. The light attenuation may be effected by replacement of the halogen lamp by a light source having a lower illuminance. However, the use of the ND filter facilitates the work of this adjustment.

Further, although the half mirror is used in the optical inspecting apparatus described in the above embodiments, this is not limitative, but a plate beam splitter of a wedge type may be used instead. In this case, a predetermined minute angle α is provided between two planes of the plate beam splitter. This makes it possible to cause ghost light generated by reflection at a transmitting surface of the plate beam splitter to be deviated out of a light path of desired light reflected from the reflecting surface, to thereby prevent the ghost light from being detected at the viewing block 7.

Further, although the optical inspecting apparatus uses a CCD in detecting an image in the above embodiments, the viewing block may be constructed such that the sample surface is viewed by way of an image formed on a screen, by camera, or by the eye. Further, in place of the CCD, there may be used any image pick-up device including a phototube, such as a photomultiplier tube.

Further, the image processing unit 5 may be adapted to perform differentiation processing, e.g. by differentiating a picture signal (original picture signal) contained in an image signal delivered from the CCD, and then adding the resulting differential signal to the original picture signal to form a new picture signal. This makes it possible to display an image in which a subtle difference in the contrast is emphasized. Further, there may be provided a brightness control circuit which makes it possible to set the brightness of an image formed by the resulting picture signal, as desired. The brightness adjustment makes it possible to easier to view the picture with brightness suitable for viewing, for example, when the state of the inside of an outline of irregularities or the outline per se is to be observed.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Apparatus for two or three dimensional inspection of a sample, said apparatus comprising:

illuminating means for illuminating a sample with an illuminating light;

an optical element for focusing light from said sample;

stop means for blocking light from irregular areas of said sample, said stop means comprising an aperture stop arranged in proximity to a back focal plane of said optical element;

a first telecentric system arranged on a back side of said aperture stop for converting light having passed through said aperture stop into a collimated light beam;

a plurality of viewing blocks optically coupled to receive said collimated light beam from said first telecentric system;

each of said viewing blocks being configured to form an image of a portion of said sample, respective portions viewed by each of said viewing blocks being different from portions viewed by others of said viewing blocks; and image processing means for synthesizing images formed by a plurality of said viewing blocks to form a single combined image of an area of said sample, said combined image having an image scale which is enlarged relative to a viewing block forming an image of all of said sample.

2. Apparatus according to claim 1, wherein said viewing block are coupled to receive said collimated light beam by means of at least one optical splitting element for splitting said collimated light beam to form a plurality of split collimated light beams, and each of said viewing blocks is coupled to receive a different one of said split collimated light beams formed by said at least one optical splitting element.

3. Apparatus according to claim 2, wherein said optical splitting element comprises a prism.

4. Apparatus according to claim 2, wherein:

said illuminating means includes a laser beam source for emitting a laser beam, and an ordinary light source for emitting an ordinary light other than said laser beam;

said optical splitting element has a selective filter for separating said laser beam and said ordinary light from each other; and at least one of said plurality of viewing blocks has means for generating optical interference fringes in response to said laser beam.

5. Apparatus according to claim 4, wherein said ordinary light is a halogen light.

6. Apparatus according to claim 2, wherein:

said illuminating means includes a laser beam source for emitting a laser beam, and an ordinary light source for emitting an ordinary light other than said laser beam;

said optical splitting element has a selective filter for separating said laser beam and said ordinary light from each other; and at least one of said plurality of viewing blocks includes a one-dimensional CCD for measuring an intensity distribution of said laser beam.

7. Apparatus according to claim 6, wherein said ordinary light source emits a halogen light.

8. Apparatus according to claim 1, further comprising a light level control signal-generating means for generating a light level control signal for setting a white level voltage or a black level voltage in an image signal of said sample to a predetermined value, and a light level control block for changing a level of light emitted from said illuminating means based on said light level control signal.

9. Apparatus according to claim 1, wherein said optical element for focusing light from said sample receives light reflected from a surface of said sample.

10. Apparatus according to claim 1 wherein each of said viewing blocks comprises a telecentric system and an aperture for limiting a portion of said sample which is viewed by said telecentric system.

11. Apparatus according to claim 1 wherein at least one of said viewing blocks is configured to form an image of all of said sample, said image having an image scale which is smaller than an image scale of said combined image.

12. Apparatus for two or three dimensional inspection of a sample, said apparatus comprising:

illuminating means for illuminating a sample with an illuminating light;

an optical element for focusing light from said sample;

stop means for blocking light from irregular areas of said sample, said stop means comprising an aperture stop arranged in proximity to a back focal plane of said optical element;

a first telecentric system arranged on a back side of said aperture stop for converting light having passed through said aperture stop into a collimated light beam;

at least one viewing block optically coupled to receive said collimated light beam from said first telecentric system;

a rotatable optical element arranged in an optical path of said collimated light beam and coupling said collimated light beam to said at least one viewing block;

an aperture element arranged in said optical path of said collimated light beam and limiting a portion of said sample which is viewed by at least a first one of said at least one viewing block; and means for causing said rotatable optical element to rotate an image of said sample contained in said collimated light beam relative to said aperture element whereby said viewing block sequentially receives images of different portions of said sample.

13. Apparatus according to claim 12 further comprising image processing means for synthesizing said images of different portions of said sample to form a single combined image of an area of said sample.

14. Apparatus according to claim 13 wherein said at least one viewing block further comprises a second viewing block which is coupled to receive said collimated light beam and to form an image of all of said sample.

15. Apparatus according to claim 14 wherein said first and second viewing blocks are coupled to receive said collimated light beam by means of at least one optical splitting element.

16. Apparatus according to claim 15 wherein each of said first and second viewing blocks comprises a telecentric system.

17. Apparatus according to claim 12 wherein said rotatable optical element is a dove prism.

* * * * *